United States Patent [19]

Carmello et al.

[11] 3,970,576

[45] July 20, 1976

[54] BACTERIOSTATIC TOILET BOWL CLEANER COMPOSITIONS

[75] Inventors: Robert Carmello, Dumont; Barry A. Salka, Clifton; Garland G. Corey, Milltown, all of N.J.

[73] Assignee: American Home Products Corporation, New York, N.Y.

[22] Filed: Mar. 21, 1975

[21] Appl. No.: 560,898

Related U.S. Application Data

[62] Division of Ser. No. 312,767, Dec. 6, 1972, Pat. No. 3,897,357.

[52] U.S. Cl. ............................................... 252/106
[51] Int. Cl.² ...................... C11D 1/72; C11D 3/48
[58] Field of Search ........... 210/64; 252/106; 4/228, 4/222; 424/347

[56] References Cited
UNITED STATES PATENTS

| | | | |
|---|---|---|---|
| 2,497,057 | 2/1950 | Pape et al. | 252/142 |
| 3,504,384 | 4/1970 | Radley et al. | 4/228 |
| 3,545,014 | 12/1970 | Davis | 4/228 |
| 3,625,903 | 12/1971 | Davies et al. | 252/107 |
| 3,630,925 | 12/1971 | Buck | 252/107 |

FOREIGN PATENTS OR APPLICATIONS

| | | |
|---|---|---|
| 2,162,790 | 7/1972 | Germany |
| 45-30706 | 5/1970 | Japan |

Primary Examiner—P.E. Willis, Jr.
Attorney, Agent, or Firm—Stephen Venetianer

[57] ABSTRACT

New automatic toilet bowl cleaner compositions that are capable of inhibiting the growth or multiplication of microbiological organisms are described herein. The bacteriostatic agent in the above compositions is 5-chloro-2-(2,4-dichlorophenoxy)phenol.

6 Claims, No Drawings

BACTERIOSTATIC TOILET BOWL CLEANER COMPOSITIONS

This is a division of application Ser. No. 312,767, filed Dec. 6, 1972, now U.S. Pat. No. 3,897,357.

BACKGROUND OF THE INVENTION

1. Field of the Invention

This invention relates to novel toilet bowl cleaner compositions. These compositions possess antimicrobial properties at the extremely low dilutions which are normally encountered with a product of this nature.

2. Description of the Prior Art

Compositions which automatically dispense cleaning agents and cleaning adjuncts into toilet bowls have been in commercial use for many years. However, the inhibition of the growth or multiplication of microbiological organisms in products of the above nature has been difficult to accomplish. This difficulty is due to the fact that most antimicrobial agents are ineffective at the extreme dilutions that automatic bowl cleaners are used.

Recently, a new antimicrobial agent, namely, 5-chloro-2-(2,4-dichlorophenoxy)phenol has been disclosed in U.S. Pat. No. 3,506,720. The assignee of this patent (Ciba-Geigy) has published data (Irgasan DP-300, Publication DC-25) which indicates that the minimum inhibitory concentration of 5-chloro-2-(2,4-dichlorophenoxy)phenol required for specific microorganisms is 1ppm for *S. aureus* and *P. mirabilis* and 3ppm for *E. coli*.

SUMMARY OF THE INVENTION

In accordance with this invention it has now been found that the use of 5-chloro-2-(2,4-dichlorophenoxy)phenol as an antimicrobial with isopropanol, an alkoxylated primary fatty alcohol and/or a linear alkyl aryl sulfonate salt combined with known dyes and perfumes produces a cleaning formulation which exhibits bacteriostatic properties against *S. aureus*, *P. mirabilis* and *E. coli* at levels as low as 0.1 per million of the antimicrobial for a solid cleaning formulation and 0.2 parts per million for a liquid cleaning formulation.

DESCRIPTION OF SPECIFIC EMBODIMENTS

The novel liquid composition of this invention comprises:

| Ingredient | % By Weight |
|---|---|
| Isopropanol | 10–20 |
| 5-chloro-2-(2,4-dichlorophenoxy)phenol | 0.5–6 |
| Alkoxylated primary fatty alcohol | 0.1–20 |
| Linear Alkyl Aryl Sulfonate Salt | 0.5–20 |
| Sodium hydroxide | 0–2 |
| Water, Dye, Perfume | Sufficient to make up to 100% |

The preferred formula for an effective liquid cleaning and bacteriostatic composition is as follows:

| Ingredient | % By Weight |
|---|---|
| Isopropanol | 14–16 |
| 5-chloro-2-(2,4-dichlorophenoxy)phenol | 1.1–1.6 |
| Alkoxylated primary fatty alcohol | 4–17 |
| Linear Alkyl Aryl Sulfonate Salt | 0.5–10 |
| Water, Dye, Perfume | Sufficient to make up to 100% |

The novel solid composition of this invention comprises:

| Ingredients | % By Weight |
|---|---|
| 5-chloro-2-(2,4-dichlorophenoxy)phenol (97% minimum activity) | 1–3 |
| Alkoxylated primary fatty alcohol | 0.1–10 |
| Ethoxylated alcohol adduct | 20–90 |
| Polyethylene glycol | 0.1–10 |
| Sodium sulfate, Perfume, Dye | Sufficient to make up to 100% |

The preferred formula for an effective solid cleaning and bacteriostatic composition is as follows:

| Ingredients | % By Weight |
|---|---|
| 5-chloro-2-(2,4-dichlorophenoxy)phenol (97% minimum activity) | 1–3 |
| Alkoxylated primary fatty alcohol | 2–8 |
| Ethoxylated alcohol adduct | 25–35 |
| Polyethylene glycol | 2–8 |
| Sodium sulfate, Perfume, Dye | Sufficient to make up to 100% |

Examples of alkoxylated primary alcohols that are useful in this invention are those alkoxylated primary alcohols wherein the alkyl chain length is primarily $C_{12}$–$C_{18}$.

Examples of linear alkyl aryl sulfonate salts that are useful in this invention are the salts of an alkyl aryl sulfonate wherein the alkyl carbon chain length is $C_1$–$C_{15}$. The novel composition in its solid form contains an ethoxylated alcohol adduct whose primary alcohol chain length is about $C_{16}$–$C_{20}$. In addition to the cleaning and bacteriostatic properties that the novel formulations of this invention possess, they also have the ability to reduce the surface tension of water.

As will be illustrated in the following examples, the liquid compositions of this invention have the ability to exhibit bacteriostatic properties at use levels as low as 0.2 parts per million of the anti-microbial. The solid compositions exhibit bacteriostatic properties at use levels as low as 0.1 parts per million of the antimicrobial. The examples will also indicate the antimicrobial agents known in the prior art are either ineffective or are not readily or efficiently compounded or solubilized.

The following examples illustrate the above described invention. The bacteria employed as the test organisms are representative of both gram negative and gram positive bacteria. The test procedure employed is the Agar Plate Test and the Agar Cup Plate Test as described in U.S.D.A. circular No. 198, 1931. The results are reported as zones of inhibition and measured in millimeters.

EXAMPLE 1

| Ingredient | % By Weight |
|---|---|
| Isopropanol (99%) | 15.00 |
| 5-chloro-2-(2,4-dichlorophenoxy)phenol (97% minimum activity) | 1.50 |
| 50% ethylene oxide>adduct 10% propylene oxide>adduct | 12.00 | of a linear alcohol whose
carbon chain length is $C_{12}-C_{15}$
Sodium Xylene Sulfonate (40%)    2.50
Water, Dye, Perfume    Sufficient to make up to 100%

Average Zone of Inhibition (mm) Dilution 1:23,000

|  | S aureus | E coli | P mirabilis |
|---|---|---|---|
| Agar Cup Plate Test | 10 | 5 | 3 |
| Agar Plate Test | 5 | 2 | 1 |

A preferred alternate formulation is represented by Example 2

EXAMPLE 2

| Ingredient | % By Weight |
|---|---|
| Isopropanol (99%) | 15.00 |
| 5-chloro-2-(2,4-dichlorophenoxy)phenol (97% minimum activity) | 1.50 |
| Triethanolaminedodecylbenzensulfonate (40%) | 15.00 |
| Water, Dye, Perfume | Sufficient to make up to 100% |

Average Zone of Inhibition (mm) Dilution 1:23,000

|  | S aureus | E coli | P mirabilis |
|---|---|---|---|
| Agar Cup Plate Test | 7 | 3 | 3 |
| Agar Plate Test | 6 | 3 | 3 |

EXAMPLE 3

| Ingredient | % By Weight |
|---|---|
| Isopropanol (99%) | 15.00 |
| 5-chloro-2-(2,4-dichlorophenoxy)phenol (97% minimum activity) | 1.50 |
| Triethanolaminedodecylbenzensulfonate (40%) | 11.25 |
| 50% ethylene oxide>adduct | 4.50 |
| 10% propylene oxide>adduct of a linear alcohol whose carbon chain length is $C_{12}-C_{15}$ | |
| Water, Dye, Perfume | Sufficient to make up to 100% |

Average Zone of Inhibition (mm) Dilution 1:23,000

|  | S aureus | E coli | P mirabilis |
|---|---|---|---|
| Agar Cup Plate Test | 7 | 15 | 2.5 |

EXAMPLE 4

| Ingredient | % By Weight |
|---|---|
| Isopropanol (99%) | 4.50 |
| n-Alkyl (60% $C_{14}$, 30% $C_{16}$, 5% $C_{12}$ and 8% $C_{18}$) Dimethyl Benzyl Ammonium Chloride | 5.00 |
| n-Alkyl (68% $C_{12}$, 32% $C_{14}$) Dimethyl Ethylbenzyl Ammonium Chloride | 5.00 |
| 50% ethylene oxide>adduct 10% propylene oxide>adduct of a linear alcohol whose carbon chain length is $C_{12}-C_{15}$ | 4.00 |
| Water, Dye, Perfume | Sufficient to make up to 100% |

Average Zone of Inhibition (mm) Dilution 1:23,000

|  | S aureus | E coli |
|---|---|---|
| Agar Cup Plate Test | 2.5 | 0 |

The above is an example of the use of another antimicrobial agent employed at a much higher level than those in the previous examples which was ineffective against E. coli.

EXAMPLE 5

| Ingredient | % By Weight |
|---|---|
| 4',5 Dibromosalicylanilide and 3,4'5, Tribromosalicylanilide (1:1 mixture) | 6.00 |
| Polyethylene Glycol (molecular weight about 200) | 50.00 |
| Octyl phenoxypoly (ethyleneoxy) Ethanol | 30.00 |
| Water | Sufficient to make up to 100% |

Average Zone of Inhibition (mm) Dilution 1:20,000

|  | S aureus | E coli |
|---|---|---|
| Agar Cup Plate Test | 16 | 11 |

The above is an example of the use of a different antimicrobial agent which requires high levels of solubilizers and which was used at higher levels itself to achieve bacteriological activity.

EXAMPLE 6

| Ingredient | % By Weight |
|---|---|
| 3,4'5 Tribromosalicylanilide | 6.00 |
| Polyethylene Glycol (molecular weight about 200) | 60.00 |
| Octyl phenoxypoly (ethyleneoxy) ethanol | 30.00 |
| Water | 4.00 |

Average Zone of Inhibition (mm) Dilution 1:20,000

|  | S aureus | E coli |
|---|---|---|
| Agar Cup Plate Test | 10 | 4 (Partial) |

This example illustrates another antimicrobial agent which requires high levels of solubilizers and which results in only a partial zone of inhibition at the high level employed.

EXAMPLE 7

| Ingredient | % By Weight |
|---|---|
| Alkyl pyridinium 5-chloro-2-mercapto-benzothiazole (96%) | 12.00 |
| N-methyl-2-pyrrolidone | 60.00 |
| Octyl phenoxy poly (ethyleneoxy) ethanol | 10.00 |
| Water | 18.00 |

Average Zone of Inhibition (mm) Dilution 1:20,000

|  | S aureus | E coli |
|---|---|---|
| Agar Cup Plate Test | 7 | 0 |

This example illustrates yet another antimicrobial agent which though used at a higher level does not result in a zone of inhibition on E. coli

EXAMPLE 8

This example illustrates the use of the solid formulation of this invention as a toilet bowl cleaner. The use dilution for microbiological activity with this composition is 0.30 parts per million of the formulation per 23,000 parts of water.

| Component | % By Weight |
|---|---|
| 100 moles of ethylene oxide adduct of a primary alcohol whose carbon length is $C_{16}-C_{20}$ | 31.00 |
| Polyethylene Glycol (molecular weight about 6,000) | 5.00 |
| 50% ethylene oxide>adduct 10% propylene oxide>adduct of a linear alcohol whose carbon chain length is $C_{12}-C_{15}$ | 5.00 |
| 5-chloro-2-(2,4-dichlorophenoxy)phenol (97% minimum activity) | 1.25 |
| Sodium Sulfate | 55.25 |
| Perfume, Dye | Sufficient to make up to 100% |

Average Zone of Inhibition (mm)

|  | S aureus | E coli | P mirabilis |
|---|---|---|---|
| Agar Cup Plate Test | 4.5 | 2 | 2.5 |

EXAMPLE 9

This Example illustrates the use of 5-chloro-2-(2,4-dichlorophenoxy)phenol in the following liquid formulation where it is present at 0.50% by weight in a use dilution of 1:23,000 and 1:40,000.

| Ingredients | % By Weight |
| --- | --- |
| Isopropanol (99%) | 15.00 |
| 5-chloro-2-(2,4-dichlorophenoxy) phenol (97% minimum activity) | 0.50 |
| 50% ethylene oxide>adduct 10% propylene oxide>adduct of a linear alcohol whose carbon chain length is $C_{12}$–$C_{15}$ | 12.00 |
| Water | 67.75 |
| Sodium Xylene Sulfonate (40%) | 2.50 |
| Dye | 1.00 |
| Perfume | 1.25 |

| Average Zone of Inhibition (mm) | S. aureus | E. coli | P. mirabilis |
| --- | --- | --- | --- |
| Agar Cup Plate Test (Dilution 1:23,000) | 6 | 2.5 | 2 |
| Agar Cup Plate Test (Dilution 1:40,000) | 4 | 1.5 | 0 |

EXAMPLE 10

| Component | % By Weight |
| --- | --- |
| Ethoxylated Alcohol Adduct | 31.00 |
| Polyethylene Glycol (mol. wt. about 6000) | 5.00 |
| Oxyethylated Alcohol Surfactant | 5.00 |
| 4',5 Dibromosalicylanilide, 3, 4'5 Tribromosalicylanilide (1:1 mixture) | 2.50 |
| Sodium Sulfate | 54.00 |
| Perfume, Dye | Sufficient to make up to 100% |

| Average Zone of Inhibition (mm) | S aureus | E coli | P mirabilis |
| --- | --- | --- | --- |
| Agar Cup Plate Test | 2.5 | 0 | 0 |

This example illustrates the use of an antimicrobial agent which does not exhibit activity in the composition.

EXAMPLE 11

| Component | % By Weight |
| --- | --- |
| Ethoxylated Alcohol Adduct | 31.00 |
| Polyethylene Glycol (mol. wt about 6000) | 5.00 |
| Oxyethylated Alcohol Surfactant | 5.00 |
| 3,4',5 Tribromosalicylanilide | 2.50 |
| Sodium Sulfate | 54.00 |
| Perfume, Dye | Sufficient to make up to 100% |

| Average Zone of Inhibition (mm) | S aureus | E coli | P mirabilis |
| --- | --- | --- | --- |
| Agar Cup Plate Test | 0 | 0 | 0 |

This example illustrates a total lack of activity of an antimicrobial in the composition.

EXAMPLE 12

The following data represents the ability of the preferred compositions of this invention to help retard stain buildup on a ceramic surface immersed in a solution containing an iron salt. Results are reported as units of stain pickup on white ceramic tiles. Less than 1 unit difference is visible to the naked eye.

| | Average Units Iron Stain Pickup | Surface Tension Dynes/CM |
| --- | --- | --- |
| Composition (Example 1) | 4.1 | 41.4 |
| Water | 5.8 | 72 |
| Composition (Example 8) | 2.5 | 33 |
| Water | 6.1 | 72 |

We claim:
1. An anti-bacterial solid composition consisting essentially of:

| Component | % By Weight |
| --- | --- |
| 5-Chloro-2-(2,4 dichlorophenoxy)phenol | 1–3 |
| Ethoxylated alcohol adduct | 20–90 |
| Alkoxylated primary fatty alcohol | 0.1–10 |
| Polyethylene glycol | 0.1–10 |
| Sodium sulfate, perfume, dye | Sufficient to make up to 100% | wherein 5-chloro-2-(2,4-dichlorophenoxy)phenol is present at a use dilution of about 0.1 parts per million to less than 1.0 parts per million, wherein the alkyl chain length of the alkoxylated primary alcohol is from about 12 carbon atoms to 15 carbon atoms and the alkyl chain length of the ethoxylated alcohol adduct is from 16 carbon atoms to about 20 carbon atoms.

2. A composition according to claim 1 wherein the components have the following proportions:

| Components | % By Weight |
| --- | --- |
| 5-Chloro-2-(2,4 dichlorophenoxy)phenol | 1–3 |
| Ethoxylated alcohol adduct | 25–35 |
| Alkoxylated primary fatty alcohol | 2–8 |
| Polyethylene glycol | 2–8 |
| Sodium sulfate, perfume, dye | Sufficient to make up to 100% |

3. A composition according to claim 1 wherein the alkoxylated primary fatty alcohol is a 50% ethylene oxide, 10% propylene oxide adduct of a linear alcohol.

4. A composition according to claim 1, wherein the polyethylene glycol has a molecular weight of approximately 6000.

5. A method for preventing the growth or multiplication of E. coli in toilet bowls which comprises dispensing into the water of a toilet an antibacterial solid composition consisting essentially of:

| Component | % By Weight |
| --- | --- |
| 5-Chloro-2-(2,4 dichlorophenoxy)phenol | 1–3 |
| Ethoxylated alcohol adduct | 20–90 |
| Alkoxylated primary fatty alcohol | 0.1–10 |
| Polyethylene glycol | 0.1–10 |
| Sodium sulfate, perfume, dye | Sufficient to make up to 100% | wherein 5-chloro-2-(2,4-dichlorophenoxy)phenol is present at a use dilution in amounts of about 0.1 parts per million to less than 3.0 parts per million, wherein the alkyl chain length of the alkoxylated primary alcohol is from about 12 carbon atoms to 15 carbon atoms and the alkyl chain length of the ethoxylated alcohol adduct is from 16 carbon atoms to about 20 carbon atoms.

6. A method for preventing the growth or multiplication of S. aureus, P. mirabilis and E. coli in toilet bowls which comprises dispensing the composition of claim 1 into the water of a toilet to prevent such growth.

* * * * *